United States Patent [19]

Leaback

[11] 4,276,048
[45] Jun. 30, 1981

[54] MINIATURE REACTION CONTAINER AND A METHOD AND APPARATUS FOR INTRODUCING MICRO VOLUMES OF LIQUID TO SUCH A CONTAINER

[75] Inventor: David H. Leaback, Radlett, England
[73] Assignee: Dynatech AG, Zug, Switzerland
[21] Appl. No.: 48,375
[22] Filed: Jun. 14, 1979
[51] Int. Cl.$^3$ .................. B01L 3/02; G01N 33/48; G01N 33/50
[52] U.S. Cl. .................. 23/230 R; 23/230 B; 73/863.32; 128/763; 128/768; 422/57; 422/65; 422/100; 435/291; 435/296
[58] Field of Search .............. 23/230 B, 230 R; 422/57, 59, 100, 69, 65; 73/425.4, 425.6; 435/291, 296; 128/763, 768

[56] References Cited

U.S. PATENT DOCUMENTS

| | | | |
|---|---|---|---|
| 2,638,787 | 5/1953 | Flaig et al. | 73/425.6 |
| 3,286,506 | 11/1966 | Lloyd | 422/59 |
| 3,388,975 | 6/1968 | Wallace | 422/59 |
| 3,660,037 | 5/1972 | Sokol | 422/100 |
| 3,716,338 | 2/1973 | Moran | 422/65 |
| 3,768,978 | 10/1973 | Grubb et al. | 422/57 |
| 3,855,867 | 12/1974 | Roach | 73/425.6 |
| 4,117,728 | 10/1978 | Johnson | 422/100 |

*Primary Examiner*—Michael S. Marcus
*Attorney, Agent, or Firm*—LeBlanc, Nolan, Shur & Nies

[57] ABSTRACT

A miniature reaction container for conducting reactions with precise micro-liter volumes of liquid reactants, reagents and samples for the purposes of enzyme assay procedures, comprises a tubular reaction chamber made from a transparent wettable plastics material and an inlet tube made from a transparent non-wettable material, such as Teflon. Both the chamber and the inlet tube may be capillary tubes and the volume of the chamber should not exceed 30 $\mu$l. For the purposes of a particular assay procedure, the chamber may be pretreated so as to have a reactant adhered or chemically bonded to its inside surface. With a plurality of such reaction containers, a multiplicity of reaction mixtures may be prepared and incubated simultaneously. To this end, the containers, which may or may not have been pretreated with reactant, are mounted in a slidable assembly together with syringes. The needles of the syringes are connected to the reaction chambers and their plungers are ganged together so as to be movable by the mechanism simultaneously to draw a precisely metered microvolume of liquid into the inlet tube of each container. By dipping the inlet tubes successively into different liquids and actuating the syringes, coherent threads of these liquids are formed in the inlet tubes and subsequently drawn into the reaction chambers to produce reaction mixtures. These reaction mixtures may be incubated within the containers before being expressed therefrom and assayed, for example, by fluorimetry.

6 Claims, 5 Drawing Figures

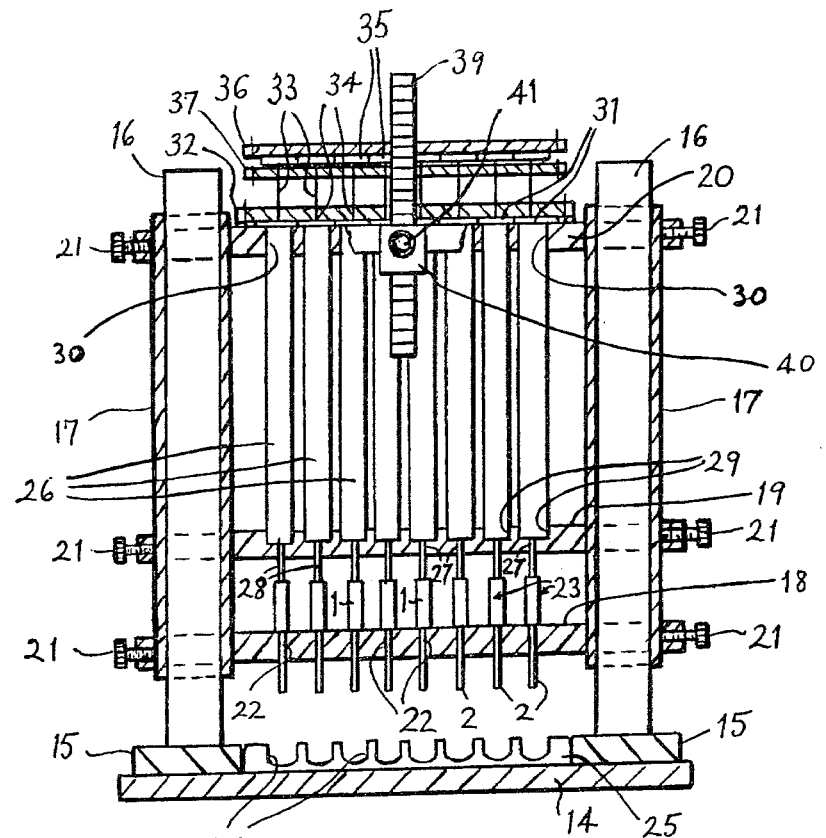
Fig. 4
Fig. 5
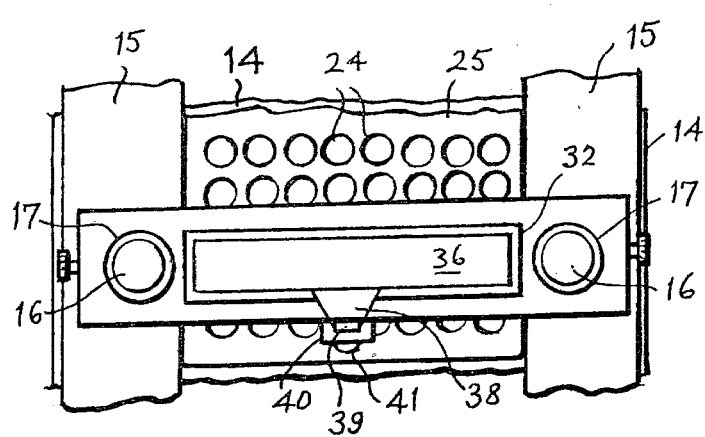

MINIATURE REACTION CONTAINER AND A METHOD AND APPARATUS FOR INTRODUCING MICRO VOLUMES OF LIQUID TO SUCH A CONTAINER

BACKGROUND OF THE INVENTION

The present invention relates to a miniature reaction container and methods and apparatus for introducing micro volumes of liquids to such a container, and its aim is to enable reactions to be conducted with micro volumes of liquid reactants, reagents and samples, more particularly, for the purposes of chemical, biochemical or biological assays which comprise a series of steps involving the production of a reaction mixture of precise micro volumes of liquids.

In assay procedures for measuring the quantity of a particular substance in a biological fluid, a precise volume of a sample is mixed with predetermined volumes of reactants and reagents. Thus, such procedures require a series of steps in which accurate volumes of liquids must be dispensed.

Automatic apparatus is available for performing these procedures although this apparatus is generally designed for dealing with large numbers of assays and is often not well suited, both in terms of time and expense, for performing individual or small numbers of assay reactions. Furthermore, such automatic apparatus is rarely adapted to analyse small samples and often uses relatively large volumes of reactants and reagents.

Some reactants, such as artificial enzyme substrates, used in assay procedures are extremely expensive and, moreover, the amount of a sample, such as body fluid, available for assaying may be very limited. Accordingly, there is a demand for a technique which will enable assay procedures or other reactions to be conducted with minute or micro volumes of reactants, reagents and samples. There is also a demand for a technique which will allow individual or small numbers of reactions to be performed and which does not require very complex apparatus or a high degree of skill and expertise on the part of an operator, whilst at the same time offering economies in the use of reactants and reagents.

SUMMARY OF THE INVENTION

It is an object of the present invention to provide a reaction container which is suitable for use in conducting reactions with micro volumes of reactants, reagents and/or samples and which is inexpensive and is designed so as accurately and easily to handle such micro volumes. Further objects of the invention are to provide a method and apparatus for delivering a precise micro volume of a liquid reactant, reagent or sample to a reaction container for the purposes of conducting a reaction and, particularly, for simultaneously delivering precise micro volumes of liquids to a multiplicity of such containers.

From one aspect, the invention consists in a miniature reaction container, comprising a tubular reaction chamber having an inlet tube at one end of the chamber substantially coaxially therewith, said inlet tube being of smaller diameter than the chamber, being in the nature of a capillary tube and being made from a non-wettable material.

The diameter of the inlet tube is such that a liquid can be sucked through the inlet tube as a coherent thread of liquid, that is, a solid column of liquid, unbroken by air or gas bubbles, when the free end of the inlet tube is open to atmosphere. It comprises a translucent non-wettable material, such as Teflon, and the bore of the tube preferably has accurately parallel sides so that a precise quantity of liquid may be introduced without extraneous drops remaining adhered to the inside or outside of the tube.

The tubular reaction chamber may be formed from any material inert to the reactants and reagents. Preferably, it is formed from a translucent wettable polymeric material, such as flexible or rigid polythene or polyvinyl chloride. As the reaction chamber is wider than the inlet tube, this stimulates mixing of reactants, reagents and samples, as they are successively drawn by suction into the reaction chamber from the inlet tube, and mixing is assisted by the wettable nature of the material from which the reaction chamber is made. However, the diameter of the reaction chamber must not be so wide that the micro volumes of liquids used separate into discrete droplets within the reaction chamber. Preferably, the diameter of the reaction chamber is also such that the micro volumes of liquid delivered to the reaction chamber may be sucked along the reaction chamber in a direction away from the inlet tube as a coherent thread of liquid.

In a typical example, the inlet tube has an internal diameter of approximately 0.6 mm. and a length of approximately 25 mm., whilst the reaction chamber has an internal diameter of approximately 1.6 mm. and a length of approximately 25 mm. The volume of the reaction chamber should not exceed 50 $\mu$l and, preferably, does not exceed 30 $\mu$l.

The reaction chamber may include an outlet tube coaxial therewith and extending from its end opposite the inlet tube for connecting the container to a source of suction, such as a syringe. The outlet tube may be of the same or similar diameter to that of the inlet tube and may be made from the same material as either the inlet tube or the chamber. Alternatively, the outlet tube may simply be the needle of a syringe attached to the container for applying suction thereto, the syringe needle being inserted into the end of the reaction chamber opposite to the inlet tube.

The reaction chamber may be integrally formed with the inlet tube or, alternatively, the inlet and/or outlet tubes may be attached to the reaction chamber via fluid tight seals. It is essential that any joints between the reaction chamber and the tube(s) be fluid-tight as the container is intended for conducting reactions with metered micro volumes of liquid which are introduced into the container by suction and any leaks would cause inaccuracies in the liquid volumes introduced.

The reaction chamber may be formed with one or more constrictions intermediate its ends in order to separate the chamber into two or more reaction zones. Thus, one reaction may be performed in a first zone and then the reaction products may be transferred by suction to the second zone which may already contain an additional reactant for conducting a second reaction, or whereupon an additional reactant may be introduced into the second zone for a second reaction. Such an arrangement is particularly advantageous for those assays which require two or more reactions before the stage is reached at which the mixture may be accurately assayed.

In another embodiment, the reaction chamber has a second tubular reaction chamber disposed at its end remote from the inlet tube and coaxial with the first tubular reaction chamber, this second chamber being of larger diameter than the first chamber.

Containers according to the present invention may be pretreated by the manufacturer and be supplied to laboratories for conducting specified reactions, tests or assays. To this end, one or more reactants may be introduced into the reaction chamber, via the inlet tube, by the manufacturer and be adhered or chemically bonded, for example, by covalent bonding, to the inside surface of the reaction chamber. A reactant may be introduced into the reaction container as a solution or dispersion and thereafter be freeze dried to adhere the solids to the inside surfaces of the chamber or the material of the chamber and the reactant may be selected so that the reactant will chemically bond, for example, covalently, to the inside surface of the chamber. A plurality of reactants or reagents may be adhered or chemically bonded to the inside surfaces of the reaction chamber or chambers at different zones along the length of the chamber(s) so as to permit two or more successive reactions to be conducted in the chamber(s). These zones may be separated by one or more constrictions or be disposed in successive chambers, as described above, or may simply be different annular zones along the cylindrical inside surface of a reaction chamber.

A particular advantage of miniature reaction containers according to the invention is that they are cheap to manufacture and they may be disposed of after use thereby avoiding extensive washing procedures which would be required if the containers had to be reused. Moreover, miniature disposable reaction containers containing one or more required reactants for a particular assay adhered to the inside of the reaction chamber may be prepared in bulk and sold. This enables a laboratory, for example a hospital laboratory, to maintain a stock of disposable reaction containers covering a wide range of differing assay reactions which may immediately be utilised for the desired assay, thereby providing a considerable saving in time.

Furthermore, the volumes of reactants and samples used in a miniature reaction chamber according to the invention may be very small, for example, 0.1 $\mu$l per aliquot of reactant and typically 2 $\mu$l per aliquot. This is particularly important when small volumes of sample are available and when expensive reactants, such as artificial enzyme substrates, are required in an assay procedure.

A further advantage of the reaction container is that various reactants, reagents or samples may be kept separate in the container until required. Thus, by a suitable choice of the length and holding capacity of the inlet tube, it is possible to form threads of different liquid reactants, reagents or sample, each separated by a volume of buffer, water or air, and the threads may be maintained in the inlet tube and be successively introduced into the reaction chamber in a preselected order, as required. Thus, an operator may position the reactants, reagents and samples in the desired manner simply by introducing them into the inlet tube in a required order.

Certain assay procedures require the mixture of reactants, reagents and/or samples to be incubated before a stage is reached at which the mixture may be assayed. Plainly, when an assay is being conducted with micro volumes of reaction liquids, these may readily evaporate upon incubation, thus prohibiting an assay. Apparatus hitherto available for conducting assay reactions has not been specifically designed for conducting reactions with micro volumes of liquids and permits undue evaporation which makes it unsuitable for this type of assay reaction. The present invention overcomes this disadvantage of the prior apparatus and permits assay reactions, which require incubation, to be conducted with micro volumes of liquids without substantial fluid loss due to evaporation. Hence, with the invention, when a mixture requiring incubation has been prepared in the reaction chamber, the inlet tube and the opposite end of the chamber may be readily sealed, for example, with paraffin wax, and the reaction container may be incubated without fluid loss. Moreover, when the incubation stage is completed, the incubated mixture may be readily discharged from the container for processing through further assay stages by merely cutting off the inlet tube and the reaction chamber at points between the seals and expressing the mixture.

From another aspect, the present invention consists in a method of introducing a micro volume of a liquid reactant, reagent or sample into a reaction container of the type described above, comprising the steps of dipping the inlet tube of the container into the liquid, applying suction to the end of the reaction chamber remote from the inlet tube so as to draw a micro volume of the liquid into the inlet tube and form a coherent thread of liquid therein, removing the inlet tube from the liquid, and applying further suction to draw the liquid into the reaction chamber of the container.

From yet another aspect, the invention consists in a method of simultaneously introducing micro volumes of liquid reactants, reagents or samples into a multiplicity of reaction containers of the type described above, comprising the steps of disposing the containers substantially upright in a predetermined array, simultaneously dipping the inlet tube of the containers into the liquid, simultaneously applying suction to the ends of the reaction chambers remote from their inlet tubes so as to draw micro volumes of the liquid into the inlet tubes and form coherent threads of liquid therein, simultaneously removing the inlet tubes from the liquid, and simultaneously applying further suction to draw the threads of liquid into the reaction chambers of the containers.

In one embodiment, the reaction containers are arranged in a row of eight containers so spaced that the inlet tubes of the containers may be simultaneously dipped into the eight wells of one row of a conventional microtest plate. Alternatively, the containers may be disposed in an array of twelve rows of eight containers so that the inlet tubes may be simultaneously dipped into all the wells of a conventional microtest plate.

Subsequently to the first suction step, the inlet tube(s) may be successively dipped into one or more further liquids and suction applied to the containers(s) so as to draw a micro volume of the or each further liquid into the inlet tube(s) for admixture in the reaction chamber(s) of the contaier(s) in the desired sequence for conducting required reactions. Alternatively, the first liquid may comprise a solution or dispersion of a first reactant or reagent which may be adhered to the inside surface of the reaction chamber(s) of the container(s) by freeze drying or chemical bonding, and the further liquid(s) may not be added until some time later when it is desired to conduct an assay reaction involving the first reactant or reagent.

When the desired reaction mixture has been produced in a reaction container, its inlet tube and the opposite end of its reaction chamber may be sealed and the reaction mixture may be incubated within the reaction chamber. Thereafter, the inlet tube may be cut so as to break the seal and the incubated reaction mixture expressed from the container into a receptacle and assayed.

When a reaction container has two or more reaction zones or chambers, the reaction mixture first produced may be sucked as a coherent thread of liquid from the first zone or chamber into a second zone or chamber, which may or may not have been pretreated with a reactant, for conducting a second reaction. When the second zone or chamber has not been pretreated, after the first reacton mixture has been drawn into the second zone or chamber, the inlet tube of the container may be dipped into yet a further liquid reactant, reagent or sample, suction is applied to the container so as to draw a micro volume of the further liquid into the inlet tube, whereafter the inlet tube is removed from the liquid and further suction is applied so as to draw the further liquid through the inlet tube and the first reaction chamber or zone into the second chamber or zone, thereby to effect mixing of the further liquid with the first reaction mixture.

From a further aspect, the present invention consists in apparatus for simultaneously introducing micro volumes of liquid reactants, reagents or samples into a multiplicity of reaction containers of the type described above disposed in a predetermined array, comprising support means for locating the containers in said predetermined array with their inlet tubes projecting downwardly, said support means being movable to dip the inlet tubes of the containers simultanesouly into one or more receptacles containing liquid disposed below the support means, and means for simultaneously applying suction to the ends of the containters opposite their inlet tubes so as to draw a predetermined micro volume of liquid from the receptacle(s) into the inlet tube of each container.

The suction means may be any device capable of accurately metering a repetitive volume of liquid. In a preferred embodiment, the suction means comprises a plurality of syringes having their needles connectable in a fluid-tight manner to the ends of the reaction containers opposite to their inlet tubes. The syringes may be ganged with their plungers coupled together so that the plungers are movable simultaneously to draw a metered volume of liquid into the inlet tube of each of the associated reaction containers. The coupled plungers may be actuated by a suitable mechanism which, upon operation, automatically withdraws each plunger by a predetermined increment, whereby to suck a predetermined miro volume of liquid into each inlet tube. Such a mechanism may comprise a rack and a pinion, a ratchet mechanism, a screw thread or other suitable mechanism for intermittently moving the plungers by predetermined increments.

The apparatus of this invention enables a multiplicity of assay reaction mixtures to be produced simultaneously with accurately metered micro volumes of liquid reactants, reagents and samples.

BRIEF DESCRIPTION OF THE DRAWINGS

In order that the invention may be more readily understood, reference will now be made to the accompanying drawings, in which :

FIG. 4 is a vertical cross-section through apparatus according to the invention for simultaneously introducing micro volumes of liquid into a multiplicity of the miniature reaction containers, and FIG. 5 is a fragmentary plan view of the apparatus.

DESCRIPTION OF THE PREFERRED EMBODIMENTS

Figures 1, 2, 3:
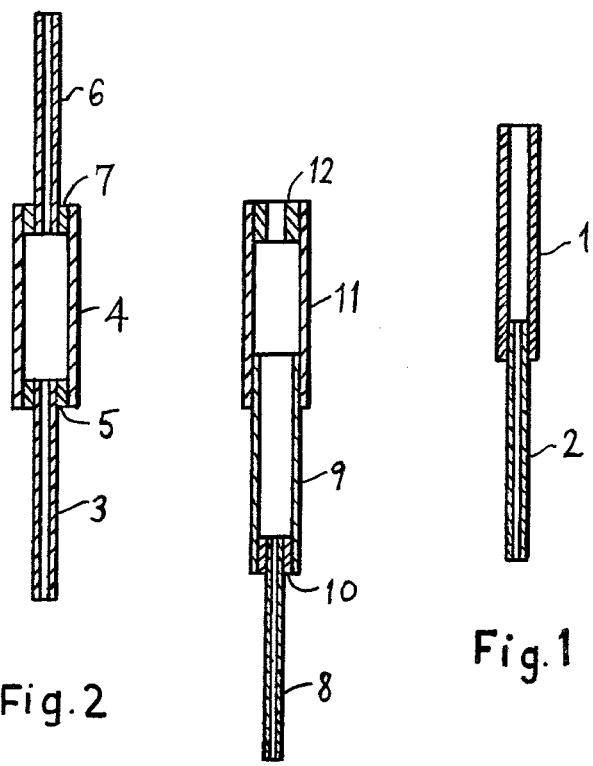
FIG. 1 is an enlarged axial section through a first embodiment of miniature reaction container according to the invention.
FIGS. 2 and 3 are enlarged axial sections through two further embodiments of the container.

FIG. 1 illustrates a simple form of miniature reaction container according to the invention. It conprises a transparent tubular reaction chamber 1 having a transparent inlet tube 2, which has a external diameter substantially equal to the internal diameter of the chamber, inserted coaxially into one end of the chamber and secured in position by adhesive. The inlet tube 2 is made from a non-wettable material, such as Teflon, whilst the chamber 1 is made from a wettable plastics material, such as polyvinyl chloride. Both the inlet tube and the reaction chamber may be defined as caillary tubes. In a typical example, the inlet tube is 0.6 mm. in diameter and the reaction chamber is 1.6 mm. in diameter and both tubes are approximately 25 mm. long. The volume of the reaction chamber should not exceed 30 $\mu$l.

The container illustrated in FIG. 2 has an inlet tube 3 of similar dimensions to the inlet tube 2 of FIG. 1 and a tubular reaction chamber 4 of slightly larger diameter than the reaction chamber 1. However, its volume does not exceed 30 $\mu$l. The inlet tube 3 is connected to the reaction chamber by means of a collar 5 which is adhered to the inlet tube and the chamber and forms a fluid-tight seal therebetween. Connected to the opposite end of the reaction chamber is an outlet tube 6 of similar dimensions to the inlet tube 3 and connected to the adjacent end of the reaction chamber in the same manner by means of a collar 7. The inlet tube 3 is made from a transparent non-wettable plastics material whilst the chamber 4 and outlet tube 6 are made from a transparent wettable plastics material. The collars 5,7 may be made from a suitable transparent plastics material, which may be the same as the inlet tube or chamber.

The container illustrated in FIG. 3 comprises a transparent non-wettable inlet tube 8, similar to the inlet tubes 2 and 3, connected to a tubular reaction chamber 9, in a fluid-tight manner, by a collar 10 in a similar manner to the inlet tube 3 of FIG. 2. Like the preceding embodiments, the tubular reaction chamber 9 is made from a transparent wettable plastics material and has a volume not exceeding 30 $\mu$l. At its upper end, the chamber 9 is secured within the bore of a length of transparent tube 11 which has an internal diameter substantially equal to the external diameter of the chamber 9 and which serves as a second tubular reaction chamber. At its upper end, the chamber 11 is constricted by a collar 12 which is sized to form a fluid-tight fit between the container and the needle of a syringe inserted into the bore of the collar 12. The chamber 11 and the collar 12 may be made from the same transparent wettable material as the chamber 9.

FIGS. 4 and 5 illustrate apparatus for simultaneously introducing metered volumes of liquid reactants, reagents or samples in micro-liter quantities into a multiplicity of miniature reaction containers according to the invention. The apparatus includes a base plate 14 having mutually parallel guide flanges 15 extending along opposite sides of the plate. Projecting upwardly from the flanges 15 are two posts 16 which slidably support tubes 17 mounting three horizontal support members or bars 18, 19, 20. These bars are adjustably fixed to the tubes 17 by set screws 21.

The lower support bar 18 has a row of eight holes 22 at equally spaced positions along the centre part of the bar and fitted through these holes are the inlet tubes 2 of eight miniature reaction containers 23 so that the bar locates the containers in a row in upright, uniformly spaced positions. The spacing of the containers is such that the inlet tubes of the containers can dip respectively into the wells 24 of a row of wells on a microtest plate 25 slidably guided on the base plate 14 between the flanges 15. Preferably, the microtest plate is mounted in a predetermined position on a carriage (not shown) slidably guided between the flanges 15 and movable in steps so as successively to index the rows of wells of the plate 25 in alignment with the inlet tubes 2.

Mounted between the bars 19,20 at a spacing conforming to the spacing of the reaction containers 23 are eight syringes 26. The middle bar 19 has a row of holes 27 coaxial with the holes 22 in the lower bar 18 for receiving the needles 28 of the syringes, which needles project through the bar 19 and are connected to the upper ends of the containers 23. The holes 27 are counterbored at 29 so as to form cavities for seating the lower ends of the syringes. At their upper ends, the syringes project through holes 30 in the upper bar 20 and have flanges 31 at their upper ends clamped between the upper surface of the bar 20 and a clamping plate 32 fastened to the bar 20 by screws. The plungers 33 of the syringes project through suitable holes 34 in the clamping plate 32 and have the disc-shaped knobs 35 at their upper ends clamped between two plates 36,37 fastened together by screws. The lower plate 37 has a projecting flange 38 which is fastened to a vertically movable rack 39 of a manually actuated ratchet mechanism 40 secured to the front end of the bar 20. The mechanism 40 is actuated by a press-button 41 and each depression of this button is adapted to advance the rack upwardly by one tooth or step and retract the plungers 33 by a predetermined increment which sucks a metered volume of fluid into each of the reaction containers 23. In one example, each depression of the button 41 retracts each of the plungers by a volume increment of 1 $\mu$l.

The reaction containers 23 may be of any of the constructions shown in FIGS. 1–3. However, by way of example only, they are illustrated in FIG. 4 as being of the construction shown in FIG. 1. The needles 28 of the syringes fit, in a fluid-tight manner, directly into the upper, open ends of the reaction chambers 1 of these containers. The latter may be pretreated so as to have a reactant, such as, an enzyme substrate, adhered to the inside surface of their reaction chambers.

In order to conduct an assay reaction, the tubes 17 are manually moved up and down the posts 16 so as successively to dip the inlet tubes 2 of the containers into different rows of wells in the microtest plate 14 containing liquid reagent and sample and, when the inlet tubes are dipped into the reagent or sample, the press button 41 is depressed so as to actuate the plungers 33 and draw a precisely metered volume of reagent or sample, measured in one or more microliters, into the inlet tubes of the containers. For example, in this way, 3 $\mu$l of water, 1 $\mu$l of buffer and 1 $\mu$l of sample may be introduced into each inlet tube of each container. When the inlet tubes 2 are dipped into the wells 24, the bottom ends of the tubes 17 abut the flanges 15 to control the dipped positions of the inlet tubes. The tubes are a frictional fit on the posts.

Subsequently to the introduction of the sample into the inlet tubes and removal of the inlet tubes from the sample liquid, the button 41 is again actuated several times in order further to retract the syringe plungers and successively suck the reactants into the reaction chambers 1 of the containers, where the reactants are mixed together. By regulating the actuation of the button 41, the reactants may either be drawn into the reaction chambers in one stage or may be drawn into the chambers at predetermined intervals. To assist the mixing process, the plungers may be slightly joggled up and down by manually moving the ratchet bar 39. The ratchet mechanism may be automatically freed when the rack 39 is manually pushed or pulled and therefore readily permits the plungers to be joggled. Thereafter, the inlet tubes 2 are sealed by drawing molten paraffin wax into the lower ends of the tubes, in the same manner as the reactants, and then the whole assembly of tubes 17, bars 18, 19, 20, containers 23 and syringes 26 is removed from the posts 16 and transferred to an incubator where the containers 23 are incubated at the desired temperature. After the incubation stage, the inlet tubes are severed above the seal and the contents are expelled by means of the syringes into a buffer which is assayed by a suitable technique, such as fluorimetry. The reaction containers 23 are thereafter removed from the assembly and disposed of and the assembly may be reused without any requirement for washing since none of the reactants, reagents or samples are drawn into the syringes.

The apparatus described above may also be used for pretreating the reaction containers so as to adhere or chemically bond a reactant to the inside surfaces of the reaction chamber 1. This is effected by mounting the containers 23 on the bar 18 with their upper ends attached to the needles of the syringes and then lowering the assembly on the posts 16 so as to dip the inlet tubes 2 into a solution or dispersion of the required reactant, either contained in the wells of a microtest plate or in a trough. The ratchet mechanism 40 is then operated so as to draw the required microliter quantities of the reactant into each inlet tube, whereupon the inlet tubes are withdrawn from the reactant and the ratchet mechanism is again operated to draw the metered volumes of reactant into the reaction chambers. The containers are then demounted from the bar 18 and treated so as to freeze dry the reactants and adhere the solids to the inside surfaces of the containers. Alternatively, if the reaction chambers are made from a suitable material, such as nylon, the reactant may be covalently bonded to the inside surfaces of the chambers. In this way, containers pretreated for use in different assay reactions may be produced in bulk.

The following is an example of an assay of an enzyme activity (in this case $\beta$-N-acetyl-D-glucosaminadase) (EC.3.21.30) which may be conducted using a reaction container according to the invention:

(i) The reaction container (having its reaction chamber charged with 40 n moles of 4-methylumbelliferyl 2-acetamido-2-deoxy-$\beta$-D-glucoside) is attached to a syringe.

(ii) Three aliquots of 2 $\mu$l of water and one 2 $\mu$l of aliquot of 0.25 M citrate buffer pH 4.3 are metered (without air gaps) up into the reaction chamber and allowed to stand until the substrate is dissolved.

(iii) One 2 μl aliquot of the enzyme solution is metered into the reaction chamber and the mixture rapidly moved into the reaction zone and mixed by slight upwards and downwards movement of the plunger of the syringe. (iv) One 2 μl aliquot of molten paraffin wax is admitted to the inlet tube and the reaction chamber incubated at 37° C.

(v) After incubation is complete the inlet tube is cut at the point above the solidifed paraffin wax and the contents of the reaction chamber voided into (200 μl of 0.2 M glycine buffer pH 10.3.

(vi) The glycine solution is assayed for 4-methylumbelliferene by fluorimetric means.

Whilst particular embodiments have been described, it will be appreciated that modifications and variations can be made without departing from the scope of the invention as defined by the appended claims.

I claim:

1. A method of conducting a chemical reaction with micro volumes of liquids, comprising the steps of:
   (a) utilizing a reaction container including a tubular reaction chamber having an inlet tube at one end of said chamber substantially coaxial therewith, said inlet tube being of smaller diameter than said chamber, being in the nature of a capillary tube and being made from non-wettable material,
   (b) successively dipping said inlet tube of said container into a plurality of liquids,
   (c) at each dipping step, applying suction to the end of said reaction chamber opposite said inlet tube to suck a precise micro volume of each said liquid into said inlet tube and form successive coherent threads of said liquids therein,
   (d) removing said inlet tube from the last one of said liquids sucked into said inlet tube, and
   (e) applying further suction to said reaction chamber in at least one stage to control successive introduction of said threads of liquid into said reaction chamber and consequent mixing of said liquids within said reaction chamber.

2. A method as claimed in claim 1, wherein said reaction container is pre-treated by adhering at least one reactant for conducting a specified reaction to the inside surface of said reaction chamber.

3. A method of simultaneously conducting a multiplicity of chemical reactions with micro volumes of liquids, comprising the steps of:
   (a) disposing a multiplicity of reaction containers in substantially upright positions in a predetermined array, each said container including a tubular reaction chamber having an inlet tube at one end of said chamber substantially coaxial therewith, said inlet tube being of smaller diameter than said chamber, being in the nature of a capillary tube and being made from non-wettable material,
   (b) simultaneously dipping said inlet tubes of said containers successively into a plurality of liquids,
   (c) at each dipping step, simultaneously applying suction to the ends of the said reaction chambers opposite their inlet tubes to suck precise micro volumes of each said liquid into said inlet tubes and form successive coherent threads of said liquids in said inlet tubes,
   (d) simultaneously removing said inlet tubes from the last one of said liquids sucked into said inlet tubes, and
   (e) simultaneously applying further suction to said reaction chambers in at least one stage to control successive introduction of said threads into said reaction chambers and consequent mixing of said liquids within said reaction chambers.

4. A method as claimed in claim 3, wherein said reaction containers are pre-treated by adhering reactants for conducting specified reactions to the inside surfaces of said reaction chambers.

5. A method as claimed in claim 3, wherein each of said reaction containers has at least two reaction zones, the reaction mixture produced in a first zone adjacent said inlet tube is sucked as a coherent thread of liquid from said first zone into a second zone, and a second reaction is conducted in said second zone.

6. A method of simultaneously conducting a multiplicity of chemical reactions with micro volumes of liquids, comprising the steps of:
   (a) disposing a multiplicity of reaction containers in substantially upright positions in a predetermined array, each said container including a tubular reaction chamber having an inlet tube at one end of said chamber substantially coaxial therewith, said inlet tube being of smaller diameter than said chamber, being in the nature of a capillary tube and being made from non-wettable material,
   (b) simultaneously dipping said inlet tubes of said containers successively into a plurality of liquids,
   (c) at each dipping step, simultaneously applying suction to the ends of said reaction chambers opposite their inlet tubes to suck precise micro volumes of each said liquid into said inlet tubes and form successive coherent threads of said liquids in said inlet tubes,
   (d) simultaneously removing said inlet tubes from the last one of said liquids sucked into said inlet tubes,
   (e) simultaneously applying further suction to said reaction chambers in at least one stage to control successive introduction of said threads of liquids into said reaction chambers and consequent mixing of said liquids within said reaction chambers,
   (f) sealing said inlet tubes and the opposite ends of said containers, incubating the resulting mixtues within said containers,
   (h) breaking said seals of said inlet tubes and expressing the incubated mixtures from said containers into receptacles, and
   (i) assaying said incubated mixtures.

* * * * *